US00PP28383P3

(12) United States Plant Patent
Verwer

(10) Patent No.: US PP28,383 P3
(45) Date of Patent: Sep. 12, 2017

(54) ***DAHLIA* PLANT NAMED 'DAHSC226'**

(50) Latin Name: *Dahlia hybrida*
Varietal Denomination: DAHSC226

(71) Applicant: Aad W. M. Verwer, Lisse (NL)

(72) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 28 days.

(21) Appl. No.: 14/998,424

(22) Filed: Dec. 31, 2015

(65) Prior Publication Data

US 2017/0196153 P1 Jul. 6, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

*Primary Examiner* — Susan McCormick Ewoldt
(74) *Attorney, Agent, or Firm* — C. A. Whealy

(57) ABSTRACT

A new and distinct cultivar of *Dahlia* plant named 'DAHSC226', characterized by its relatively compact, mounding and dense plant habit; freely basal branching habit; dark green-colored leaves; early and freely flowering habit; double-type inflorescence form; large inflorescences with white and purple bi-colored ray florets; and good postproduction longevity and garden performance.

2 Drawing Sheets

Botanical designation: *Dahlia hybrida.*
Cultivar denomination: 'DAHSC226'.

BACKGROUND OF THE INVENTION

The present invention relates to a new and distinct cultivar of *Dahlia* plant, botanically known as *Dahlia hybrida*, and hereinafter referred to by the name 'DAHSC226'.

The new *Dahlia* plant is a product of a planned breeding program conducted by the Inventor in Lisse, The Netherlands. The objective of the breeding program is to create new compact container and garden *Dahlia* plants with dark-colored leaves, large inflorescences and good postproduction longevity.

The new *Dahlia* plant originated from a cross-pollination conducted by the Inventor during the summer of 2010 of *Dahlia hybrida* 'Maya', not patented, as the female, or seed, parent with *Dahlia hybrida* 'Oriental Dream', not patented, as the male, or pollen, parent. The new *Dahlia* plant was discovered and selected by the Inventor as a single flowering plant from within the progeny of the stated cross-pollination in a controlled greenhouse environment in Lisse, The Netherlands during the summer of 2011.

Asexual reproduction of the new *Dahlia* plant by cuttings since the spring of 2012 in a controlled greenhouse environment in Lisse, The Netherlands, has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'DAHSC226'. These characteristics in combination distinguish 'DAHSC226' as a new and distinct *Dahlia* plant:

1. Relatively compact, mounding and dense plant habit.
2. Freely basal branching habit.
3. Dark green-colored leaves.
4. Early and freely flowering habit.
5. Double-type inflorescence form.
6. Large inflorescences with white and purple bi-colored ray florets.
7. Good postproduction longevity and garden performance.

Plants of the new *Dahlia* differ primarily from plants of the female parent, 'Maya', in the following characteristics:

1. Plants of the new *Dahlia* are denser than and not as open as plants of 'Maya'.
2. Plants of the new *Dahlia* are more freely branching than plants of 'Maya'.
3. Plants of the new *Dahlia* and 'Maya' differ in ray floret color as plants of 'Maya' have apricot-colored ray florets.

Plants of the new *Dahlia* differ primarily from plants of the male parent, 'Oriental Dream', in the following characteristics:

1. Leaves of plants of the new *Dahlia* are lighter in color than leaves of plants of 'Oriental Dream'.
2. Plants of the new *Dahlia* have larger inflorescences than plants of 'Oriental Dream'.

Plants of the new *Dahlia* can be compared to plants of the *Dahlia hybrida* 'Karma Amanda', disclosed in U.S. Plant Pat. No. 11,399. In side-by-side comparisons conducted in Lisse, The Netherlands, plants of the new *Dahlia* differed from plants of 'Karma Amanda' in the following characteristics:

1. Plants of the new *Dahlia* were more compact than plants of 'Karma Amanda'.

2. Plants of the new *Dahlia* were more branching than plants of 'Karma Amanda'.
3. Plants of the new *Dahlia* had larger inflorescences than plants of 'Karma Amanda'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet comprises a side perspective view of a typical flowering plant of 'DAHSC226' grown in an outdoor nursery.

The photograph on the second sheet is a close-up view of a typical flowering plant of 'DAHSC226'.

DETAILED BOTANICAL DESCRIPTION

The photographs and following observations and measurements describe plants grown during the late summer and early autumn in ground beds in an outdoor nursery in Lisse, The Netherlands and under cultural practices typical of commercial *Dahlia* production. During the production of the plants, day temperatures ranged from 12° C. to 28° C. and night temperatures ranged from 6° C. to 23° C. Plants were pinched one time about three weeks after planting. Plants were three months old when the photographs and the description were taken In the following description, color references are made to The Royal Horticultural Society Colour Chart, 1995 Edition, except where general terms of ordinary dictionary significance are used.

Botanical classification: *Dahlia hybrida* 'DAHSC226'.

Parentage:

*Female, or seed, parent.*—*Dahlia hybrida* 'Maya', not patented.

*Male, or pollen, parent.*—*Dahlia hybrida* 'Oriental Dream', not patented.

Propagation:

*Type.*—By vegetative cuttings.

*Time to initiate roots, summer and winter.*—About five at temperatures about 17° C.

*Time to produce a rooted young plant, summer.*—About 14 days at temperatures about 17° C.

*Time to produce a rooted young plant, winter.*—About 17 days at temperatures about 17° C.

*Root description.*—Fine; initially fibrous becoming fleshy with development.

*Rooting habit.*—Moderately freely branching; dense.

*Tubers.*—Length: About 15 cm. Diameter: About 14 cm. Texture: Corky. Color: Close to 164D.

Plant description:

*Plant and growth habit.*—Relatively compact and mounding plant habit; appropriate for 20-cm to 25-cm containers; inverted triangular plant form; freely basal branching with about seven primary lateral branches developing per plant; dense and bushy appearance; inflorescences held above the foliar plane on strong peduncles; vigorous growth habit.

*Plant height.*—About 65 cm.

*Plant diameter or spread.*—About 40 cm.

*Lateral branches.*—Length: About 60 cm. Diameter: About 9 mm. Internode length: About 4 cm to 7 cm. Texture: Smooth, glabrous. Strength: Strong. Aspect: Erect to about 15° from vertical. Color: Close to 145A.

Leaf description:

*Arrangement.*—Opposite, simple or compound with three or five leaflets per leaf.

*Leaf length, simple leaves.*—About 12 cm.

*Leaf width, simple leaves.*—About 6 cm.

*Leaf length, compound leaves with three leaflets.*—About 15 cm.

*Leaf width, compound leaves with three leaflets.*—About 6 cm.

*Leaf length, compound leaves with five leaflets.*—About 26 cm.

*Leaf width, compound leaves with five leaflets.*—About 6 cm.

*Shape, simple leaves or leaflets.*—Ovate.

*Apex, simple leaves or leaflets.*—Acuminate.

*Base, simple leaves or leaflets.*—Attenuate.

*Margin, simple leaves or leaflets.*—Serrulate; sinuses divergent.

*Venation pattern, simple leaves or leaflets.*—Pinnate, reticulate.

*Texture, upper and lower surfaces, simple leaves or leaflets.*—Smooth, glabrous.

*Color.*—Developing and fully expanded leaves or leaflets, upper surface: Close to 137A; venation, close to 148B. Developing and fully expanded leaves or leaflets, lower surface: Close to 148B; venation, close to 146A.

*Petioles.*—Length, simple leaves: About 1.5 cm. Width, simple leaves: About 4 mm. Length, compound leaves with three leaflets: About 2 cm. Diameter, compound leaves with three leaflets: About 4 mm. Length, compound leaves with five leaflets: About 6 cm. Diameter, compound leaves with five leaflets: About 7 mm. Texture, upper and lower surfaces, simple leaves or leaflets: Smooth, glabrous. Color, simple leaves or leaflets, upper and lower surfaces: Close to 145A.

Inflorescence description:

*Appearance and flowering habit.*—Double-type inflorescences with ray and disc florets developing acropetally on a receptacle; inflorescences roughly hemispherical in shape; inflorescences positioned above and beyond the foliar plane on strong peduncles; inflorescences face upright to outwardly; freely flowering habit with typically about 28 inflorescence buds and open inflorescences per plant at one time during the flowering season.

*Fragrance.*—None detected.

*Time to flower.*—Early flowering habit; plants begin flowering about 65 days after planting; flowering continuous during the summer and autumn in The Netherlands.

*Post-production longevity.*—Good postproduction longevity; inflorescences maintain good substance for about 20 days on the plant and for about seven days as a cut flower; inflorescences persistent.

*Inflorescence buds.*—Height: About 1.6 cm. Diameter: About 2.2 cm. Shape: Oblate. Texture: Smooth, glabrous. Color: Towards the base, close to 146B; mid-section, close to 151A; towards the apex, close to 64B.

*Inflorescence diameter*.—Large, about 16 cm.

*Inflorescence depth* (*height*).—About 7 cm.

*Disc diameter*.—About 8 mm, inconspicuous.

*Receptacle height*.—About 2.3 cm.

*Receptacle diameter*.—About 2.2 cm.

*Ray florets*.—Number of ray florets per inflorescence: About 160 arranged in about 19 to 20 whorls. Length: About 5.4 cm. Width: About 2.1 cm. Shape: Ovate. Apex: Acute. Base: Attenuate. Margin: Entire. Aspect: Initially upright to roughly perpendicular to the peduncle and eventually outer ray florets reflexing. Texture and luster, upper and lower surfaces: Smooth, glabrous; velvety. Color: When opening, upper surface: Close to 64A. When opening, lower surface: Close to 71A. Fully opened, upper surface: Towards the base, close to 157B; mid-section, close to 75B; margins and towards the apex, close to 70B; with development, white color becomes more dominant. Fully opened, lower surface: Towards the base, close to 157B; margins and towards the apex, close to 70B; with development, white color becomes more dominant.

*Disc florets*.—Number of disc florets per inflorescence: About ten. Length: About 5 mm. Diameter: About 4 mm. Shape: Tubular; apex dentate, pentafid. Aspect: Mostly upright. Texture: Smooth, glabrous. Color, immature: Apex: Close to 12A. Mid-section: Close to 12D. Base: Close to 1C. Color, mature: Apex: Close to 16A. Mid-section: Close to 12D. Base: Close to 1C.

*Phyllaries*.—Quantity per inflorescence: About eight arranged in a single whorl. Length: About 1.5 cm. Width: About 8 mm. Shape: Ovate. Apex: Acute to acuminate. Base: Attenuate. Margin: Entire. Texture, upper and lower surfaces: Smooth, glabrous. Color, upper and lower surfaces: Close to 138A.

*Peduncles*.—Length, terminal peduncle: About 11 cm. Length, fourth peduncle: About 7 cm. Length, seventh peduncle: About 5 cm. Diameter: About 4 mm. Strength: Strong. Aspect: Mostly erect to 10° from vertical. Texture: Smooth, glabrous. Color: Close to 146C; towards the apex, tinged with close to 183A.

*Reproductive organs*.—Androecium, present on disc florets only: Quantity per disc floret: Five. Filament length: About 4.6 mm. Filament color: Close to 9B. Anther length: About 3 mm. Anther shape: Lanceolate. Anther color: Close to 17C. Pollen amount: Scarce. Pollen color: Close to 17A. Gynoecium, present on ray and disc florets: Quantity per floret: One. Pistil length: About 4 mm. Stigma shape: Lanceolate. Stigma color: Close to 12C. Style length: About 3 mm. Style color: Close to 1B. Ovary color: Close to 9D. Seeds: Seed development has not been observed on plants of the new *Dahlia*.

Disease & pest resistance: Plants of the new *Dahlia* have not been shown to be resistant to pathogens and pests common to *Dahlia* plants.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'DAHSC226' as illustrated and described.

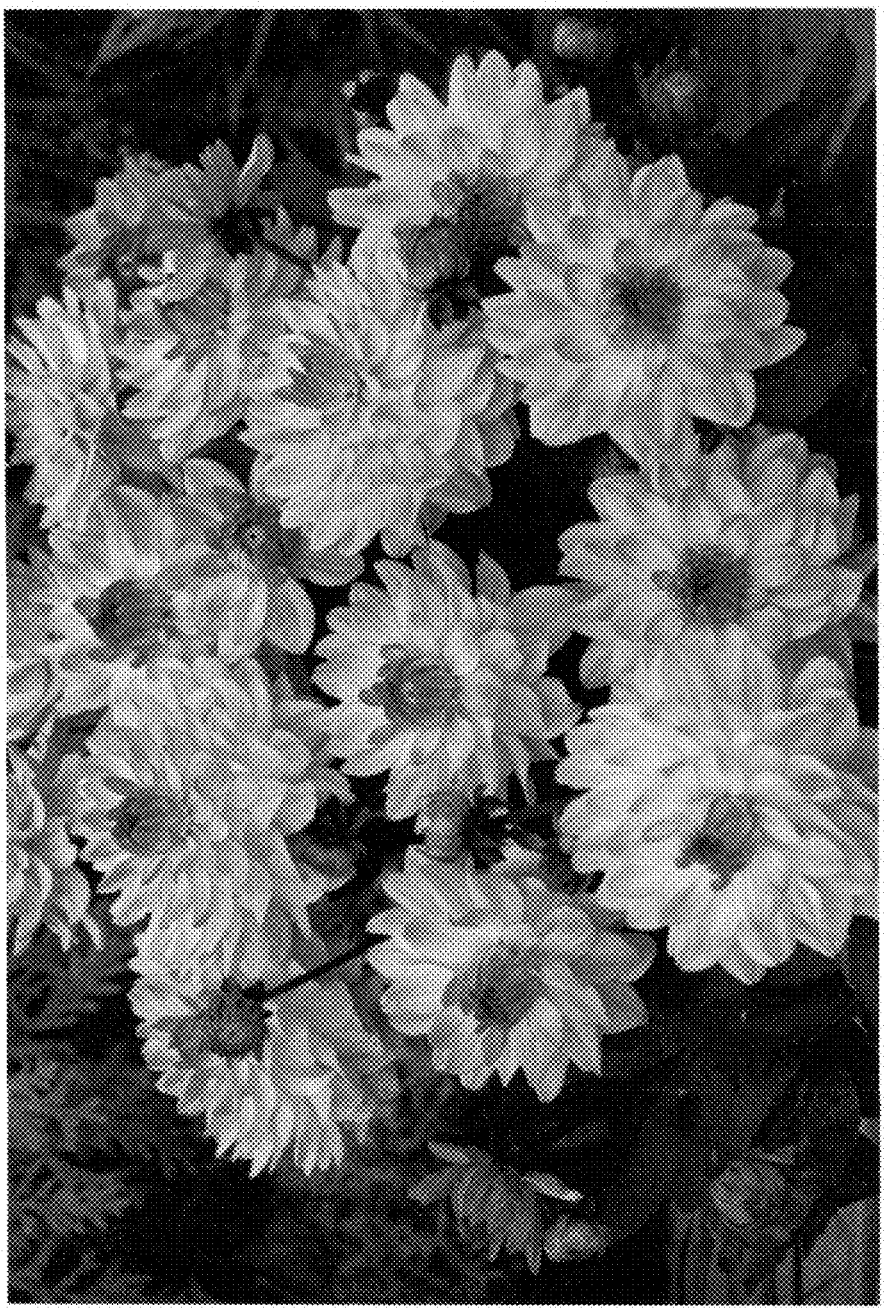

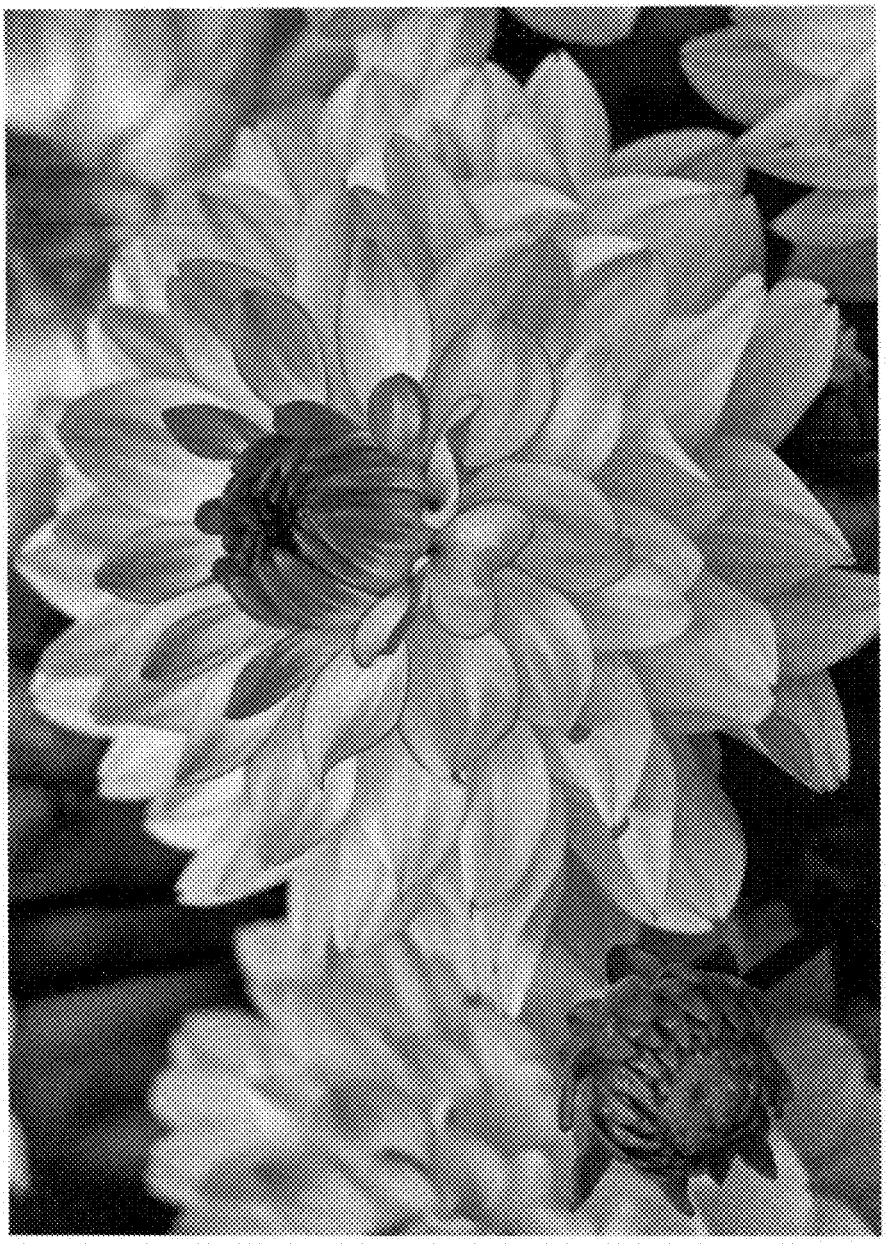

* * * * *